（12）United States Patent
Augier et al.

(10) Patent No.: US 11,492,304 B2
(45) Date of Patent: Nov. 8, 2022

(54) PROCESS FOR OLIGOMERIZATION IN A CASCADE OF STIRRED GAS-LIQUID REACTORS WITH STAGED INJECTION OF ETHYLENE

(71) Applicant: IFP Energies Nouvelles, Rueil-Malmaison (FR)

(72) Inventors: Frederic Augier, Rueil-Malmaison (FR); Alexandre Vonner, Rueil-Malmaison (FR); Tiago Sozinho, Rueil-Malmaison (FR); Natacha Touchais, Rueil-Malmaison (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 17/256,786

(22) PCT Filed: Jun. 21, 2019

(86) PCT No.: PCT/EP2019/066444
§ 371 (c)(1),
(2) Date: Dec. 29, 2020

(87) PCT Pub. No.: WO2020/002141
PCT Pub. Date: Jan. 2, 2020

(65) Prior Publication Data
US 2021/0107846 A1    Apr. 15, 2021

(30) Foreign Application Priority Data

Jun. 29, 2018 (FR) ...................................... 1856051

(51) Int. Cl.
*C07C 2/32* (2006.01)
*B01J 19/00* (2006.01)
(Continued)

(52) U.S. Cl.
CPC ............. *C07C 2/32* (2013.01); *B01J 19/0013* (2013.01); *B01J 19/245* (2013.01);
(Continued)

(58) Field of Classification Search
CPC ......... C07C 2/32; C07C 11/08; C07C 11/107; C07C 2531/12; C07C 2531/22;
(Continued)

(56) References Cited

U.S. PATENT DOCUMENTS 4,615,998 A    10/1986   Le Quan et al.
4,834,949 A     5/1989   Owen et al.
(Continued)

FOREIGN PATENT DOCUMENTS

CN    105693448 A    6/2016
EP      1710013 A1   10/2006
(Continued)

OTHER PUBLICATIONS

International Search Report PCT/EP2019/066444 dated Aug. 16, 2019 (pp. 1-3).

*Primary Examiner* — Ali Z Fadhel
(74) *Attorney, Agent, or Firm* — Millen, White, Zelano and Branigan, P.C.; Harry B. Shubin

(57) ABSTRACT

The invention relates to a process for the oligomerization of ethylene, carried out at a pressure of between 0.1 and 10.0 MPa, at a temperature of between 30 and 200° C., in a cascade of N gas/liquid reactors in series, N being at least equal to 2, comprising a step of introducing a catalytic oligomerization system into at least the first reactor of the cascade, a step of bringing said catalytic system and an optional solvent into contact with ethylene by introducing said ethylene into the lower part of the reaction chamber of at least the first reactor of the cascade, for each reactor n, a step of withdrawing a liquid fraction in the lower part of the
(Continued)

reaction chamber of the reactor n, the liquid fraction being separated into two streams: a first stream corresponding to a first, "main", part of the liquid fraction, which is conveyed to a heat exchanger for cooling; a second stream corresponding to the second part of the liquid fraction which constitutes the liquid feedstock of the following reactor n+1 in the cascade, a step of introducing said second part of the liquid phase withdrawn from the reactor n towards the reaction chamber of the following reactor n+1 in the direction of flow, a step of cooling said first part of the liquid fraction withdrawn from the reactor n in step c) by passing said first part of the liquid fraction into a heat exchanger in order to obtain a cooled liquid fraction, a step of introducing said liquid fraction cooled in step e) at the top of the reaction chamber of said reactor n, the steps a) to f) being carried out, unless indicated otherwise, for each reactor n of the cascade, n being between 1 and N. The invention also relates to a device of N stirred gas/liquid reactors in a cascade, enabling the oligomerization process to be carried out.

13 Claims, 2 Drawing Sheets

(51) Int. Cl.
  *B01J 19/24* (2006.01)
  *C07C 11/08* (2006.01)
  *C07C 11/107* (2006.01)
(52) U.S. Cl.
  CPC ............. *B01J 2219/00087* (2013.01); *B01J 2219/00105* (2013.01); *C07C 11/08* (2013.01); *C07C 11/107* (2013.01); *C07C 2531/12* (2013.01); *C07C 2531/22* (2013.01); *C07C 2531/34* (2013.01)
(58) Field of Classification Search
  CPC .... C07C 2531/34; C07C 7/06; B01J 19/0013; B01J 19/245; B01J 2219/00087; B01J 2219/00105; B01J 4/004
  See application file for complete search history.

(56) References Cited

U.S. PATENT DOCUMENTS

| | | | |
|---|---|---|---|
| 8,618,342 | B2 | 12/2013 | Guillon et al. |
| 9,096,486 | B2 | 8/2015 | Gildenhuys |
| 9,931,622 | B2 | 4/2018 | Magna et al. |
| 10,150,108 | B2 | 12/2018 | Magna et al. |
| 10,646,860 | B2 | 5/2020 | Breuil et al. |
| 2009/0209797 | A1 | 8/2009 | Moustafa et al. |
| 2013/0158321 | A1 | 6/2013 | Olivier-Bourbigou et al. |
| 2016/0229766 | A1 | 8/2016 | Sydora et al. |
| 2017/0081256 | A1* | 3/2017 | Kreischer ............. C07C 2/26 |
| 2018/0318819 | A1 | 11/2018 | Breuil et al. |

FOREIGN PATENT DOCUMENTS

| | | | |
|---|---|---|---|
| FR | 2552079 | A1 | 3/1985 |
| FR | 2959736 | A1 | 11/2011 |
| FR | 2984311 | A1 | 6/2013 |
| FR | 3019064 | A1 | 10/2015 |
| FR | 3023183 | A1 | 1/2016 |
| FR | 3042989 | A1 | 5/2017 |
| FR | 3045414 | A1 | 6/2017 |
| WO | 09060342 | A2 | 5/2009 |

* cited by examiner

PROCESS FOR OLIGOMERIZATION IN A CASCADE OF STIRRED GAS-LIQUID REACTORS WITH STAGED INJECTION OF ETHYLENE

TECHNICAL FIELD

The present invention relates to an oligomerization process employing a particular reaction device; in particular, the process relates to the oligomerization of ethylene to give linear alpha-olefins, such as but-1-ene, hex-1-ene or oct-1-ene, or a mixture of linear alpha-olefins.

PRIOR ART

The invention relates to the field of oligomerization processes employing gas/liquid reactors, also referred to as bubble point reactors.

For a given operating pressure and temperature, the performance of such a bubble point reactor in terms of selectivity for olefins and of conversion of the ethylene are limited by the kinetic scheme inherent to the catalytic system and to the operating conditions under consideration: the different main and secondary, parallel and/or consecutive reactions, the temperature and the pressure, etc. This performance ceiling may be represented by the curve for selectivity as a function of the conversion (see FIG. 1), which it is impossible to exceed without changing reactor technology.

The processes of the prior art, employing a single bubble point reactor, as illustrated in FIG. 2, do not make it possible to simultaneously achieve high levels of selectivity for olefins and of conversion of the ethylene.

Surprisingly, the applicant has discovered an implementation of the process which makes it possible to achieve higher levels of selectivity and of conversion and also to limit the implementation cost thereof. In particular, the process makes it possible to obtain linear olefins, and preferably alpha-olefins.

SUBJECT OF THE INVENTION

The subject of the present invention is therefore that of providing a process for the oligomerization of ethylene, carried out at a pressure of between 0.1 and 10.0 MPa, a temperature of between 30 and 200° C. and preferentially of between 35 and 150° C., in a cascade of N stirred gas/liquid reactors, each one being or not being able to be fed with gaseous ethylene.

SUMMARY OF THE INVENTION

The invention relates to a process for the oligomerization of ethylene, carried out at a pressure of between 0.1 and 10.0 MPa, at a temperature of between 30 and 200° C., in a cascade of N gas/liquid reactors in series, N being at least equal to 2, comprising the following steps:

a. a step of introducing a homogeneous catalytic oligomerization system comprising at least one metal precursor, optionally at least one activator and optionally at least one additive into at least the first reactor of the cascade, b. a step of bringing said catalytic system and an optional solvent into contact with ethylene by introducing said ethylene into the lower part of the reaction chamber of at least the first reactor of the cascade, c. for each reactor n, a step of withdrawing a liquid fraction in the lower part of the reaction chamber of the reactor n, the liquid fraction being separated into two streams: a first stream corresponding to a first, "main", part of the liquid fraction, which is conveyed to a heat exchanger for cooling; a second stream corresponding to the second part of the liquid fraction which constitutes the liquid feedstock of the following reactor n+1 in the cascade, d. a step of introducing said second part of the liquid phase withdrawn from the reactor n towards the reaction chamber of the following reactor n+1 in the direction of flow, comprising a liquid phase and a gas phase, e. a step of cooling said first part of the liquid fraction withdrawn from the reactor n in step c) by passing said first part of the liquid fraction into a heat exchanger in order to obtain a cooled liquid fraction, f. a step of introducing said liquid fraction cooled in step e) at the top of the reaction chamber of said reactor n, the steps a) to f) being carried out, unless indicated otherwise, for each reactor n of the cascade, n being between 1 and N.

For the final reactor N of the cascade, said second part corresponds to the effluent obtained at the end of the oligomerization process and may be conveyed to a separation section to separate the linear olefins produced.

In step b), the gaseous ethylene is preferably introduced at a flow rate of between 1 and 250 t/h.

In step b), a stream of gaseous hydrogen may be introduced into the reaction chamber, with a flow rate representing 0.2 to 1.0% by weight of the flow rate of the incoming ethylene.

In step c), the withdrawal flow rate of the liquid fraction is advantageously between 500/N and 12 000/N t/h, where N is the number of reactors in the cascade.

In step c), the flow rate of said second stream is advantageously 5 to 200 times lower than the liquid flow rate of the first stream conveyed to the cooling step.

Preferably, the cascade comprises from 2 to 10 gas/liquid reactors.

The number of reactors of the cascade which are fed with gaseous ethylene may represent between 25% and 100% of the total number of reactors in the cascade.

Advantageously, the flow rate of the liquid recirculation loop of each reactor is between 500/N and 10 000/N t/h, where N is the number of reactors in the cascade.

Preferably, the concentration of catalyst in the catalytic system is between 0.1 and 50 ppm by weight of atomic metal relative to the reaction mass.

Preferably, the catalytic oligomerization reaction is carried out continuously.

In step f), the introduction flow rate of the cooled liquid fraction is advantageously between 500/N and 10 000/N t/h, where N is the number of reactors in the cascade.

Preferably, the linear olefins obtained comprise from 4 to 12 carbon atoms.

Very preferably, the linear olefins obtained are linear alpha-olefins chosen from but-1-ene, hex-1-ene or oct-1-ene.

The invention also relates to a device for carrying out the process for the oligomerization of ethylene described above, comprising a cascade of N stirred gas/liquid reactors, each of the N reactors comprising:

a reaction chamber i), of elongated shape along the vertical axis, comprising a liquid phase, dissolved ethylene, the catalytic system and an optional solvent, and a gas phase located above said liquid phase, comprising unreacted ethylene and also the non-condensable gases;

an optional means for introducing ethylene ii), located in the lateral lower part of said reaction chamber, employing a means for distributing ethylene within said liquid phase of the reaction chamber, the feeding of gaseous ethylene being always active in the first reactor of the cascade;

an optional means for introducing the catalytic system iii) comprising at least one metal precursor, optionally at least one activator and optionally at least one additive, said means being located in the lower part of the reaction chamber, the introduction of the catalytic system being always carried out in the first reactor of the cascade and optionally in the following reactors;

a recirculation loop iv) comprising at least one withdrawal means at the base of the reaction chamber for withdrawing and conveying a first part of the liquid fraction towards a heat exchanger enabling the cooling of said cooled liquid fraction, and a means for introducing said cooled liquid fraction into the gas phase at the top of the reaction chamber, means for feeding liquid v) by the second part of the liquid fraction withdrawn from the reactor upstream in the cascade, except for the first reactor of the cascade.

DEFINITIONS & ABBREVIATIONS

Throughout the description, the terms or abbreviations below have the following meaning.

Oligomerization means any addition reaction of a first olefin with a second olefin identical to or different from the first olefin. The olefin thus obtained is of $C_nH_{2n}$ type, where n is equal to or greater than 4.

Alpha-olefin means an olefin in which the double bond is located at the terminal position of the alkyl chain.

Selective oligomerization ~~or obtaining~~ means obtaining at least 80% by weight of a desired linear alpha-olefin such as but-1-ene, hex-1-ene or oct-1-ene relative to the weight of all the olefins formed.

Catalytic system means the mixture of at least one metal precursor, optionally of at least one activating agent, and optionally of at least one additive, optionally in a solvent.

Homogeneous catalytic system means the fact that the catalytic system is in the same phase as the reactants and the products of the oligomerization reaction.

Liquid phase means the mixture of all the compounds which are in the liquid physical state under the temperature and pressure conditions of the reactor.

Gas phase or else gas headspace means the mixture of all the compounds which are in the gas physical state under the temperature and pressure conditions of the reactor: in the form of bubbles present in the liquid, and also in the top part of the reactor (the reactor headspace).

Lateral lower part of the reaction chamber means a part of the reactor casing located in the bottom portion and at the side.

Non-condensable gas means an entity in gaseous physical form which only partially dissolves in the liquid under the temperature and pressure conditions of the process and which can, under certain conditions, accumulate in the reactor headspace (the example here is ethane).

t/h means the value of a flow rate expressed as tonne per hour.

Dispersion of the liquid fraction means the significant increase in the exchange surface area between said liquid fraction and the gaseous or liquid fraction into which it is injected.

DETAILED DESCRIPTION OF THE INVENTION

It is specified that, throughout this description, the expression "between . . . and . . . " should be understood as including the mentioned limits.

For the purposes of the present invention, the various embodiments presented may be used alone or in combination with each other, without any limit to the combinations.

Figure 1:
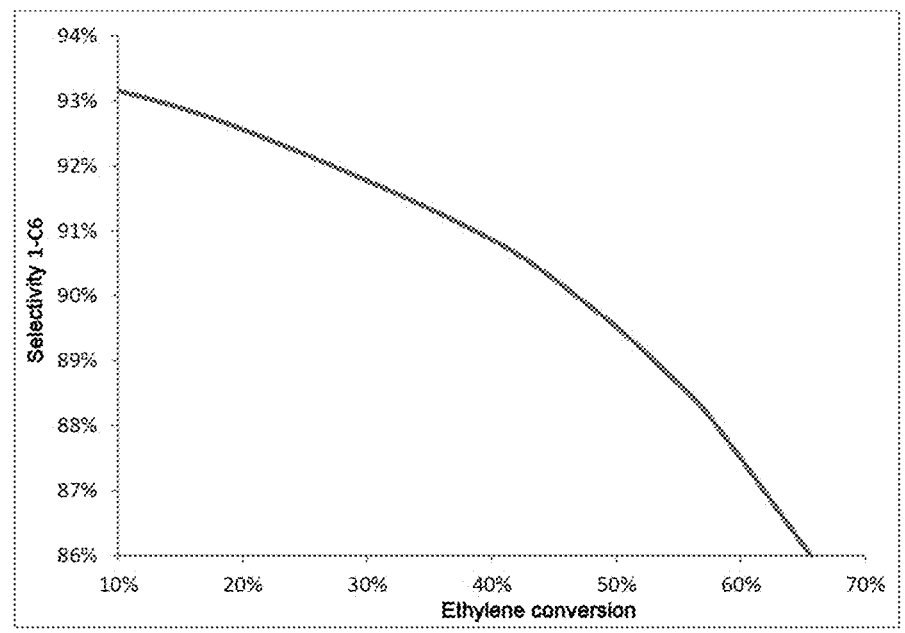
FIG. 1 depicts the selectivity for C6 olefin as a function of the conversion of ethylene in a stirred gas/liquid reactor employing an oligomerization reaction.

FIG. 1 illustrates the maximum performance limit in terms of conversion of ethylene (in % ethylene converted) and of selectivity for the desired linear olefin (in %), for the case of a stirred gas/liquid reactor for the oligomerization of ethylene. It is observed that it is not possible to achieve a high level of conversion at the same time as a high selectivity for linear olefin.

Figure 2:
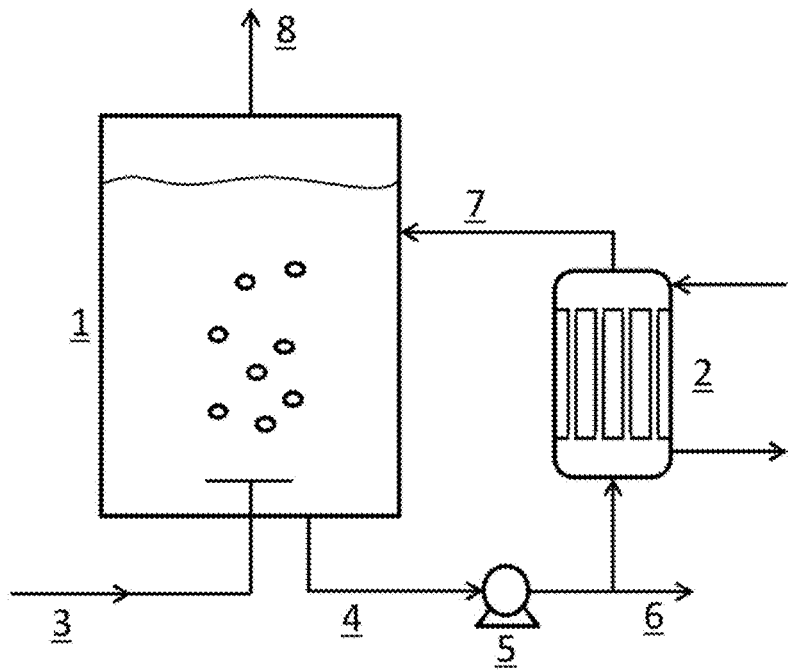
FIG. 2 illustrates a reaction device according to the prior art consisting of a single gas/liquid reactor of bubble column type with injection of gaseous ethylene and with a liquid recirculation where the heat produced by the reaction is extracted.

FIG. 2 illustrates a reaction device according to the prior art. It consists of a single gas/liquid reactor (1) of bubble column type, with injection of gaseous ethylene by injection means (3). Withdrawal means (4) make it possible, by virtue of a liquid recirculation pump (5), to convey a part of the liquid stream withdrawn to a heat exchanger (2) which makes it possible to recover the energy produced by the reaction and to feed, with cooled liquid, the top of the gas/liquid reactor via means for introducing the cooled liquid (7). The gas/liquid reactor comprises means for bleeding off the gas headspace (8) at the top of the reaction chamber.

A subject of the present invention is that of providing a process for the oligomerization of ethylene, carried out at a pressure of between 0.1 and 10.0 MPa, at a temperature of between 30 and 200° C. and preferentially of between 35 and 150° C., in an improved device consisting of a cascade of N gas/liquid reactors in series, each one being or not being able to be fed with gaseous ethylene, the first reactor being always fed with gaseous ethylene. The reaction is carried out in the presence of a catalytic oligomerization system comprising at least one metal precursor, optionally at least one activator and optionally at least one additive. The homogeneous catalytic oligomerization systems known to those skilled in the art are suitable for carrying out the process according to the invention.

Figure 3:
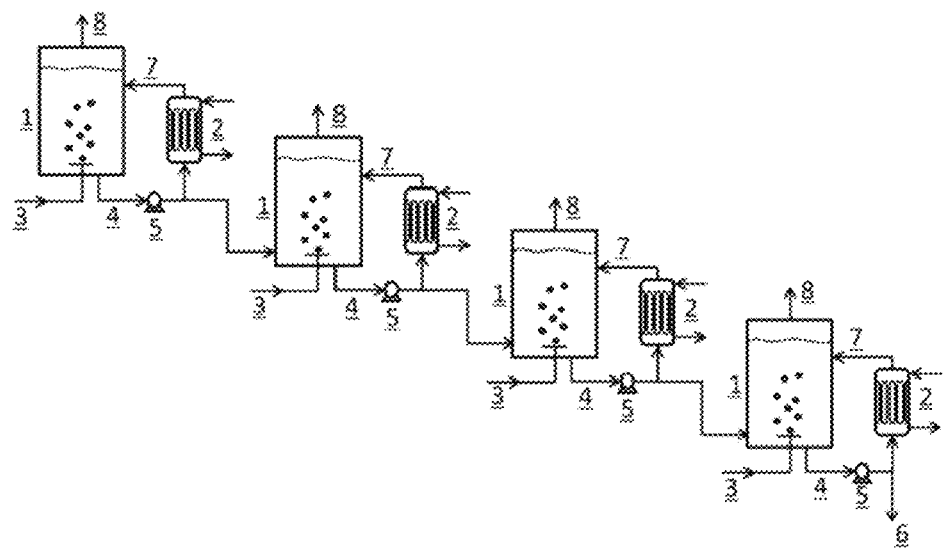
FIG. 3 illustrates a device making it possible to carry out the process according to the invention, consisting of a cascade in series of 4 stirred gas/liquid reactors of bubble column type, connected to one another by a liquid stream originating from the previous reaction chamber in the direction of flow, with flow from upstream towards downstream, in a first embodiment in which all the reactors are fed with gaseous ethylene.
Figure 4:
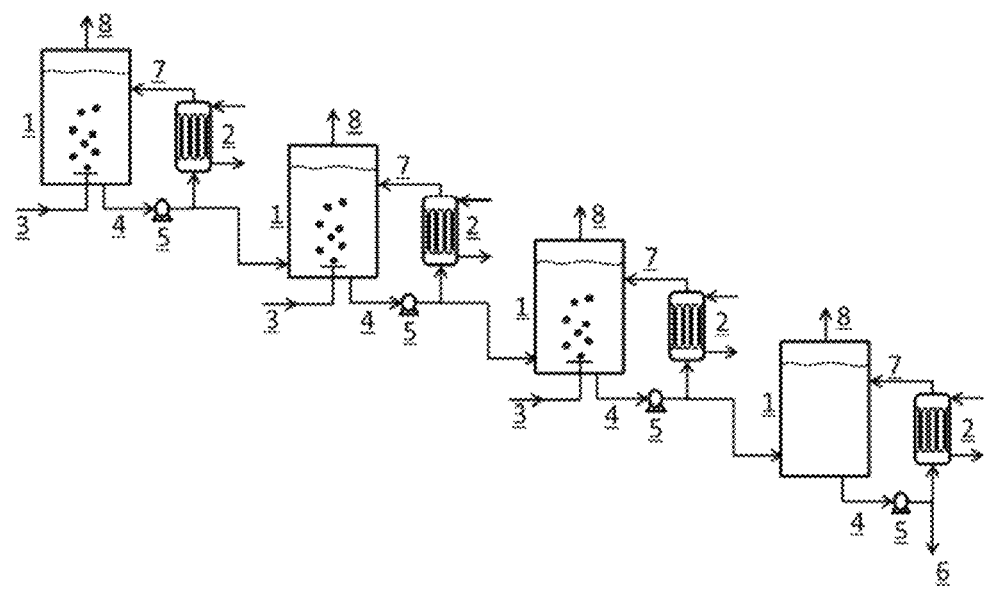
FIG. 4 illustrates a second device making it possible to carry out the process according to the invention. It differs from the device of FIG. 3 by the absence of injection of gaseous ethylene into the final reactor of the cascade.

FIGS. 3 and 4 describe two embodiments of the device and process according to the invention, employing a cascade of 4 stirred gas/liquid reactors, also referred to as bubble columns. In the embodiment of FIG. 3, all the reactors of the cascade are fed with gaseous ethylene. In the embodiment of FIG. 4, the fourth reactor (the last of the cascade) is not fed with gaseous ethylene.

The oligomerization process employs, in a cascade of 4 stirred gas/liquid reactors (1), the following steps:
- a) a step of introducing the homogeneous catalytic system into at least the first reactor (1) of the cascade;
- b) a step of bringing said catalytic system and an optional solvent into contact with ethylene. The introduction of said gaseous ethylene is carried out by injection means (3) located in the lower part of the reaction chamber of the reactors nos. 1, 2, 3 and 4 (FIG. 3) or of the reactors nos. 1, 2 and 3 (FIG. 4);
- c) a step of withdrawing a liquid fraction in the lower part of the reaction chamber, preferably by withdrawal means (4) in the bottom of the reaction chamber of each of the reactors. By virtue of a liquid recirculation pump (5), a first part of said withdrawn liquid fraction is conveyed to an external heat exchanger (2); the second part constitutes the liquid feedstock of the following reactor in the cascade in the direction of flow or the effluent of the oligomerization process (6) in the case of the 4th and final reactor of the cascade;
- d) a step of introducing said second part of the liquid fraction withdrawn from the previous reactor into the reaction chamber comprising a liquid phase and a gas phase of each of the reactors 2, 3 and 4;
- e) for each of the reactors n, a step of cooling said first part of the liquid fraction withdrawn in step c) by passing said first part of the withdrawn liquid fraction into a heat exchanger in order to obtain a cooled liquid fraction;
- f) a step of introducing said liquid fraction cooled in step e) by liquid introduction means (7) at the top of the reaction chamber of said same reactor n;
- g) in the case of the final reactor of the cascade, the withdrawn liquid part not conveyed to the heat exchanger (2) constitutes the effluent (6) obtained at the end of the oligomerization process, which may be conveyed to a separation section located downstream of the device according to the invention.

An advantage of the present invention is improving the conversion of ethylene or the selectivity for olefins, and also the volumetric productivity of the oligomerization process.

The withdrawal means (4) with the liquid recirculation pump (5), the exchanger (2) and the pipe for introducing the cooled liquid (7) constitute a liquid recirculation loop for each of the 4 reactors, making it possible to carry out the steps c), e) and f) of withdrawing a liquid fraction, cooling a part of this liquid fraction and introducing this cooled liquid fraction part at the top of the reaction chamber. Each of the four reactors of the cascade also comprises means for bleeding off (8) the non-condensable gases in the gas headspace.

The flow rate of the liquid recirculation loop of each reactor n is advantageously between 125 and 2500 t/h (i.e. 500/4 and 10 000/4 t/h, where N=4 is the number of reactors in series).

More generally the present invention relates to a process for the oligomerization of gaseous ethylene by homogeneous catalysis carried out at a pressure of between 0.1 and 10 MPa, at a temperature of between 30 and 200° C., and preferentially between 35 and 150° C., in the presence of a homogeneous catalytic oligomerization system comprising at least one metal precursor, optionally at least one activator and at least one additive in a cascade of N gas/liquid reactors in series, each of the reactors n being or not being able to be fed with gaseous ethylene, the first reactor of the cascade being always fed with gaseous ethylene, N being at least equal to 2, comprising the following steps:
- a) a step of introducing the homogeneous catalytic system into at least the first reactor of the cascade,
- b) a step of bringing said catalytic system and an optional solvent into contact with ethylene by introducing said gaseous ethylene into the lower part of the reaction chamber of at least the first reactor of the cascade,
- c) for each reactor n, a step of withdrawing a liquid fraction in the lower part of the reaction chamber of the reactor n, preferably in the bottom of the reaction chamber, the liquid fraction being separated into two streams: a first, "main", part is conveyed to an exchanger for cooling; a second part constitutes the liquid feedstock of the following reactor n+1 in the cascade,
- d) for each reactor n+1 (that is to say for each reactor except the first in the series), a step of introducing said second part of the liquid phase withdrawn from the previous reactor n in the cascade,
- e) a step of cooling the first part of the liquid fraction withdrawn from the reactor n in step c) by passing said first part of the liquid fraction into a heat exchanger in order to obtain a cooled liquid fraction,
- f) a step of introducing said liquid fraction cooled in step e) at the top of the reaction chamber of said reactor n,
- g) in the case of the final reactor of the cascade, said second part corresponds to the effluent obtained at the end of the oligomerization process and may be conveyed to a separation section located downstream of the device employed in the process according to the invention.

Oligomerization Process

The process according to the invention makes it possible to selectively obtain a linear alpha-olefin by bringing gaseous ethylene into contact with a homogeneous catalytic system and optionally in the presence of a solvent in a cascade of N gas/liquid reactors, N being at least equal to 2.

According to the invention, all the N reactors in series are gas/liquid reactors, also referred to as bubble columns.

The process according to the invention has a selectivity for a desired linear alpha-olefin of greater than 80% by weight of desired linear alpha-olefin relative to the total weight of olefins formed, preferably greater than 90% and with preference greater than 95%. Preferably, the linear alpha-olefin is chosen from but-1-ene, hex-1-ene or oct-1-ene.

The process according to the invention advantageously exhibits a conversion of gaseous ethylene of greater than 50%, preferably greater than 55%, with preference greater than 60% and very preferably greater than 65%.

Any homogeneous catalytic system known to those skilled in the art and capable of being employed in the dimerization, trimerization or tetramerization processes and more generally in the oligomerization processes according to the invention falls within the scope of the invention. Said catalytic systems and also their implementations are described in particular in Applications FR 2 984 311, FR 2

552 079, FR 3 019 064, FR 3 023 183, FR 3 042 989 or also in Application FR 3 045 414.

Preferably, the catalytic systems comprise, preferably consist of:
- a metal precursor, preferably based on nickel, on titanium or on chromium,
- an activating agent,
- optionally an additive, and
- optionally a solvent.

The Metal Precursor

The metal precursor used in the catalytic system is chosen from compounds based on nickel, on titanium or on chromium.

In one embodiment, the metal precursor is based on nickel and preferentially comprises nickel with a (+II) oxidation state. Preferably, the nickel precursor is chosen from nickel (II) carboxylates, such as, for example, nickel 2-ethylhexanoate, nickel(II) phenates, nickel(II) naphthenates, nickel(II) acetate, nickel(II) trifluoroacetate, nickel(II) triflate, nickel(II) acetylacetonate, nickel(II) hexafluoroacetylacetonate, π-allylnickel(II) chloride, π-allylnickel(II) bromide, methallylnickel(II) chloride dimer, $\eta^3$-allylnickel(II) hexafluorophosphate, $\eta^3$-methallylnickel(II) hexafluorophosphate and nickel(II) 1,5-cyclooctadienyl, in their hydrated or non-hydrated form, taken alone or as a mixture.

In a second embodiment, the metal precursor is based on titanium and preferentially comprises a titanium aryloxy or alkoxy compound.

The titanium alkoxy compound advantageously corresponds to the general formula [Ti(OR)$_4$] in which R is a linear or branched alkyl radical. Mention may be made, among the preferred alkoxy radicals, as nonlimiting examples, of tetraethoxy, tetraisopropoxy, tetra(n-butoxy) and tetra(2-ethylhexyloxy).

The titanium aryloxy compound advantageously corresponds to the general formula [Ti(OR')$_4$] in which R' is an aryl radical substituted or unsubstituted by alkyl or aryl groups. The R' radical can comprise heteroatom-based substituents. The preferred aryloxy radicals are chosen from phenoxy, 2-methylphenoxy, 2,6-dimethylphenoxy, 2,4,6-trimethylphenoxy, 4-methylphenoxy, 2-phenylphenoxy, 2,6-diphenylphenoxy, 2,4,6-triphenylphenoxy, 4-phenylphenoxy, 2-(tert-butyl)-6-phenylphenoxy, 2,4-di(tert-butyl)-6-phenylphenoxy, 2,6-diisopropylphenoxy, 2,6-di(tert-butyl)phenoxy, 4-methyl-2,6-di(tert-butyl)phenoxy, 2,6-dichloro-4-(tert-butyl)phenoxy and 2,6-dibromo-4-(tert-butyl)phenoxy, the biphenoxy radical, binaphthoxy or 1,8-naphthalenedioxy.

According to a third embodiment, the metal precursor is based on chromium and preferentially comprises a chromium(II) salt, a chromium(III) salt or a salt with a different oxidation state which can comprise one or more identical or different anions, such as, for example, halides, carboxylates, acetylacetonates or alkoxy or aryloxy anions. Preferably, the chromium-based precursor is chosen from CrCl$_3$, CrCl$_3$(tetrahydrofuran)$_3$, Cr(acetylacetonate)$_3$, Cr(naphthenate)$_3$, Cr(2-ethylhexanoate)$_3$ or Cr(acetate)$_3$.

The concentration of nickel, of titanium or of chromium is between 0.01 and 300.0 ppm by weight of atomic metal relative to the reaction mass, preferably between 0.02 and 100.0 ppm, preferentially between 0.03 and 50.0 ppm, more preferentially between 0.5 and 20.0 ppm and more preferentially still between 2.0 and 50.0 ppm by weight of atomic metal relative to the reaction mass.

The Activating Agent

Regardless of the metal precursor, the catalytic system additionally comprises one or more activating agents chosen from aluminium-based compounds, such as methylaluminium dichloride (MeAlCl$_2$), dichloroethylaluminium (EtAlCl$_2$), ethylaluminium sesquichloride (Et$_3$Al$_2$Cl$_3$), chlorodiethylaluminium (Et$_2$AlCl), chlorodiisobutylaluminium (i-Bu$_2$AlCl), triethylaluminium (AlEt$_3$), tripropylaluminium (Al(n-Pr)$_3$), triisobutylaluminium (Al(i-Bu)$_3$), diethylethoxyaluminium (Et$_2$AlOEt), methylaluminoxane (MAO), ethylaluminoxane and modified methylaluminoxanes (MMAO).

The Additive

Optionally, the homogeneous catalytic system comprises one or more additives.

When the catalytic system is based on nickel, the additive is chosen from:
- compounds of nitrogenous type, such as trimethylamine, triethylamine, pyrrole, 2,5-dimethylpyrrole, pyridine, 2-methylpyridine, 3-methylpyridine, 4-methylpyridine, 2-methoxypyridine, 3-methoxypyridine, 4-methoxypyridine, 2-fluoropyridine, 3-fluoropyridine, 3-trifluoromethylpyridine, 2-phenylpyridine, 3-phenylpyridine, 2-benzylpyridine, 3,5-dimethylpyridine, 2,6-di(tert-butyl)pyridine and 2,6-diphenylpyridine, quinoline, 1,10-phenanthroline, N-methylpyrrole, N-butylpyrrole, N-methylimidazole, N-butylimidazole, 2,2'-bipyridine, N,N'-dimethylethane-1,2-diimine, N,N'-di(t-butyl)ethane-1,2-diimine, N,N'-di(t-butyl)butane-2,3-diimine, N,N'-diphenylethane-1,2-diimine, N,N'-bis(2,6-dimethylphenyl)ethane-1,2-diimine, N,N'-bis(2,6-diisopropylphenyl)ethane-1,2-diimine, N,N'-diphenylbutane-2,3-diimine, N,N'-bis(2,6-dimethylphenyl)butane-2,3-diimine or N,N'-bis(2,6-diisopropylphenyl)butane-2,3-diimine, or
- compounds of phosphine type independently chosen from tributylphosphine, triisopropylphosphine, tricyclopentylphosphine, tricyclohexylphosphine, triphenylphosphine, tris(o-tolyl)phosphine, bis(diphenylphosphino)ethane, trioctylphosphine oxide, triphenylphosphine oxide or triphenyl phosphite, or
- compounds corresponding to the general formula (I) or one of the tautomers of said compound:

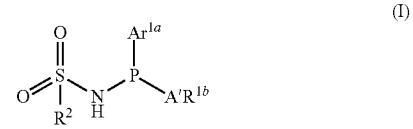

(I)

in which:
- A and A', which are identical or different, are independently an oxygen or a single bond between the phosphorus atom and a carbon atom,
- the $R^{1a}$ and $R^{1b}$ groups are independently chosen from the methyl, trifluoromethyl, ethyl, n-propyl, isopropyl, n-butyl, isobutyl, t-butyl, pentyl, cyclohexyl or adamantyl groups, which are substituted or unsubstituted and contain or do not contain heteroelements; the phenyl, o-tolyl, m-tolyl, p-tolyl, mesityl, 3,5-dimethylphenyl, 4-(n-butyl)phenyl, 2-methylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di(tert-butyl)-4-methoxyphenyl, 4-chlorophenyl, 3,5-di(trifluoromethyl)phenyl, benzyl, naphthyl, bisnaphthyl, pyridyl, bisphenyl, furanyl or thiophenyl groups, the R² group is independently chosen from the methyl, trifluoromethyl, ethyl, n-propyl, isopropyl, n-butyl, isobutyl, t-butyl, pentyl, cyclohexyl or adamantyl groups, which are substituted or unsubstituted and contain or do not contain heteroelements; the phenyl, o-tolyl, m-tolyl, p-tolyl, mesityl, 3,5-dimethylphenyl, 4-(n-butyl)phenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di(tert-butyl)-4-methoxyphenyl, 4-chlorophenyl, 3,5-bis(trifluoromethyl)phenyl, benzyl, naphthyl, bisnaphthyl, pyridyl, bisphenyl, furanyl or thiophenyl groups.

When the catalytic system is based on titanium, the additive is chosen from diethyl ether, diisopropyl ether, dibutyl ether, diphenyl ether, 2-methoxy-2-methylpropane, 2-methoxy-2-methylbutane, 2,2-dimethoxypropane, 2,2-di(2-ethylhexyloxy)propane, 2,5-dihydrofuran, tetrahydrofuran, 2-methoxytetrahydrofuran, 2-methyltetrahydrofuran, 3-methyltetrahydrofuran, 2,3-dihydropyran, tetrahydropyran, 1,3-dioxolane, 1,3-dioxane, 1,4-dioxane, dimethoxyethane, di(2-methoxyethyl) ether, benzofuran, glyme and diglyme, taken alone or as a mixture.

When the catalytic system is based on chromium, the additive is chosen from:
aryloxy compounds of general formula $[M(R^3O)_{2-n}X_n]_y$, in which:
M is chosen from magnesium, calcium, strontium and barium, preferably magnesium; preferably, M is magnesium,
$R^3$ is an aryl radical containing from 6 to 30 carbon atoms and X is a halogen or an alkyl radical containing from 1 to 20 carbon atoms,
n is an integer which can take the values of 0 or 1, and y is an integer of between 1 and 10; preferably, y is equal to 1, 2, 3 or 4.

Preferably, the aryloxy radical $R^3O$ is chosen from 4-phenylphenoxy, 2-phenylphenoxy, 2,6-diphenylphenoxy, 2,4,6-triphenylphenoxy, 2,3,5,6-tetraphenylphenoxy, 2-(tert-butyl)-6-phenylphenoxy, 2,4-di(tert-butyl)-6-phenylphenoxy, 2,6-diisopropylphenoxy, 2,6-dimethylphenoxy, 2,6-di(tert-butyl)phenoxy, 4-methyl-2,6-di(tert-butyl)phenoxy, 2,6-dichloro-4-(tert-butyl)phenoxy and 2,6-dibromo-4-(tert-butyl)phenoxy. The two aryloxy radicals can be carried by one and the same molecule, such as, for example, the biphenoxy radical, binaphthoxy or 1,8-naphthalenedioxy. Preferably, the aryloxy radical $R^3O$ is 2,6-diphenylphenoxy, 2-(tert-butyl)-6-phenylphenoxy or 2,4-di(tert-butyl)-6-phenylphenoxy.

Preferably, when the catalytic system is based on chromium, the additive also comprises a compound of cyclic ether type. Preferably, said compound is chosen from diethyl ether, dibutyl ether, diisopropyl ether, 2-methoxy-2-methylpropane, 2-methoxy-2-methylbutane, 2,5-dihydrofuran, tetrahydrofuran, 2-methoxytetrahydrofuran, 2-methyltetrahydrofuran, 3-methyltetrahydrofuran, 2,3-dihydropyran, tetrahydropyran, 1,3-dioxolane, 1,3-dioxane, 1,4-dioxane, dimethoxyethane, di(2-methoxyethyl) ether and benzofuran, taken alone or as a mixture. Preferably, the additive is dibutyl ether.

The Solvent

In another embodiment according to the invention, the catalytic system optionally comprises one or more solvents.

The solvent or solvents are advantageously chosen from ethers, alcohols, halogenated (fluorinated, chlorinated, brominated or iodinated) solvents and aliphatic and cycloaliphatic hydrocarbons comprising between 1 and 20 carbon atoms, preferably between 2 and 10 carbon atoms, preferably between 4 and 8,
aromatic hydrocarbons comprising from 4 to 20 carbon atoms and preferably between 5 and 15 carbon atoms.

Preferably, the solvent is chosen from pentane, hexane, cyclohexane, methylcyclohexane, heptane, butane or isobutane, 1,5-cyclooctadiene, cyclopentadiene, benzene, toluene, ortho-xylene, mesitylene, ethylbenzene, diethyl ether, tetrahydrofuran, 1,4-dixoane, dichloromethane, chlorobenzene, methanol, ethanol, pure or in a mixture, and ionic liquids.

The solvent is chosen from the group formed by aliphatic and cycloaliphatic hydrocarbons, such as hexane, cyclohexane, heptane, butane or isobutane.

Preferably, the solvent used is cyclohexane.

In one embodiment, a solvent or a mixture of solvents may be used during the oligomerization reaction. Said solvent is advantageously chosen independently from the group formed by aliphatic and cycloaliphatic hydrocarbons, such as hexane, cyclohexane, heptane, butane or isobutane. Preferably, said solvent or mixture of solvents is introduced only into the first reactor of the cascade.

The oligomerization process is carried out at a pressure between 0.1 and 10.0 MPa, and preferentially between 0.3 and 8.0 MPa, at a temperature of between 30 and 200° C. and preferentially between 35 and 150° C.

The device making it possible to carry out the process according to the invention advantageously consists of a cascade of 2 to 10 gas/liquid reactors, preferably a cascade of 2 to 8 reactors, preferably a cascade of 2 to 6 reactors, preferably a cascade of 3 to 6 reactors, and with preference a cascade of 2, 3, 4 or 5 reactors. The number of these reactors which are fed with gaseous ethylene preferably represents between 25% and 100% of the total number of reactors in the cascade, very preferably between 50% and 100%.

The content by weight of solvent introduced into the cascade of reactors employed in the process according to the invention is between 0.5 and 10.0, preferably between 1.0 and 5.0, and with preference between 2.0 and 4.0. Advantageously, said contents by weight of solvent make it possible to obtain high levels of productivity. The content of solvent is the ratio by weight of the total flow rate of injected solvent to the total flow rate of injected gaseous ethylene in the process.

The flow rate of the liquid recirculation loop of each reactor is advantageously between 500/N and 10 000/N t/h, and preferably between 800/N and 7000/N t/h, where N is the number of reactors in the cascade.

Preferably, the concentration of catalyst in the catalytic system is between 0.1 and 50 ppm by weight of atomic metal relative to the reaction mass, and preferably between 0.5 and 20 ppm by weight of atomic metal relative to the reaction mass.

According to one embodiment, the catalytic oligomerization reaction is carried out continuously.

In the case of the reactors of the cascade comprising an injection of ethylene, the catalytic solution, composed as described above, is injected at the same time as the ethylene into the stirred reactor(s) by conventional mechanical means known to those skilled in the art or by an external recirculation, and kept at the desired temperature. It is also possible to inject the components of the catalyst separately into the reaction medium. The ethylene is introduced by an intake valve under the control of the pressure, which keeps the latter constant in the reactor. The reaction mixture is withdrawn by means of a valve under the control of the liquid level, so as to keep the latter constant. Except for the first reactor of the cascade, which is not fed in this way, the reaction liquid originating from the previous reactor in the cascade is introduced directly into the reaction chamber in the bottom or top part, with the possibility of using an element for dispersing the liquid phase, or is injected into the recirculation loop.

In the case of the reactors of the cascade not comprising injection of ethylene, the system is identical except for the absence of injected gas.

At the outlet of the final reactor of the cascade, the catalyst is advantageously destroyed continuously by any usual means known to those skilled in the art, and then the products resulting from the reaction, and also the solvent, are separated, for example by distillation. The ethylene which has not been converted can be recycled into the sequence of reactors. The residues of catalyst included in a heavy fraction can be incinerated.

Step a) of Introducing the Homogeneous Catalytic System

The process according to the invention comprises, at least for the first reactor of the cascade and optionally for the following reactor(s), a step a) of introducing the homogeneous catalytic system and optionally a solvent or a mixture of solvents into the reaction chamber comprising a liquid phase and a gas phase.

Preferably, the homogeneous catalytic system is introduced in the lower part of the reaction chamber and preferably in the bottom of the reaction chamber.

In a preferred embodiment, the catalytic system, optionally in the presence of a solvent or a mixture of solvents, is introduced solely into the first reactor of the cascade.

In another preferred embodiment, the catalytic system, optionally in the presence of a solvent or a mixture of solvents, is introduced into all of the reactors of the cascade. Preferably, the pressure of introduction into the reaction chamber is between 0.1 and 10.0 MPa, preferably between 0.3 and 8.0 MPa.

Preferably, the temperature of introduction into the reaction chamber is between 30 and 200° C., preferably between 35 and 150° C.

Step b) of Bringing into Contact with the Gaseous Ethylene

The process according to the invention comprises a step b) of bringing the catalytic system introduced in step a) into contact with the gaseous ethylene. Said gaseous ethylene is introduced at the lower part of the reaction chamber, preferably on the lateral lower part of the reaction chamber, in at least the first reactor of the cascade. Each of the N reactors or a part of the N reactors may be fed with gaseous ethylene, the first reactor always being fed with gaseous ethylene. In a particular embodiment, the gaseous ethylene is not introduced into the final reactor N of the cascade.

The number of reactors which are fed with gaseous ethylene represents between 25% and 100% of the total number of reactors in the cascade, preferably between 50% and 100%.

Preferably, the gaseous ethylene is distributed by dispersion during the introduction thereof into the lower liquid phase of the reaction chamber by a means able to carry out said dispersion uniformly over the whole cross section of the reactor. Preferably, the dispersion means is chosen from a distributing system with a homogeneous distribution of the points for injection of ethylene over the entire cross section of the reactor.

Preferably, the gaseous ethylene is introduced at a flow rate of between 1 and 250 t/h, preferably between 3 and 200 t/h, preferably between 5 and 150 t/h and preferably between 10 and 100 t/h.

According to a particular embodiment of the invention, a stream of gaseous hydrogen can also be introduced into the reaction chamber, with a flow rate representing 0.2 to 1.0% by weight of the flow rate of incoming ethylene. Preferably, the stream of gaseous hydrogen is introduced by the means employed for the introduction of the gaseous ethylene.

Step c) of Withdrawing a Fraction of the Liquid Phase

The process according to the invention comprises a step c) of withdrawing a fraction of the liquid phase in the lower part of the reaction chamber of each reactor n.

The withdrawal carried out in step c) is performed in the lower part of the reaction chamber of the reactor n, preferably below the level of the ethylene injection, and preferably in the bottom of the chamber. The withdrawal is carried out by any means capable of carrying out the withdrawal and preferably by using a pump.

Preferably, the withdrawal flow rate is between 500/N and 12 000/N t/h, and preferably between 800/N and 8500/N t/h, where N denotes the number of reactors of the cascade.

The liquid fraction withdrawn from the liquid phase is divided into two streams. A first, "main", stream is conveyed to the cooling step e). For all the reactors of the cascade apart from the final reactor, the second stream is conveyed to the step d) of introduction into the reactor located downstream in the cascade. In the case of the final reactor of the cascade, the second stream corresponds to the effluent obtained at the end of the oligomerization process and may be conveyed to a separation section located downstream of the device employed in the process according to the invention.

Regardless of the reactor in question in the cascade, the flow rate of the second stream is advantageously regulated so as to keep a constant liquid level in the reactor. The flow rate of said second stream is advantageously lower than the flow rate of said first, "main", stream.

Preferably, the flow rate of said second stream is 5 to 200 times lower than the liquid flow rate of the main stream conveyed to the cooling step. Very preferably, the flow rate of said second stream is 5 to 150 times lower, preferably 10 to 120 times lower and with preference 20 to 100 times lower.

Step d) of Introducing the Liquid Fraction Originating from the Previous Reactor in the Cascade The process according to the invention comprises a step d) of introducing the second part of the liquid fraction withdrawn from the previous reactor in the cascade into the reaction chamber of the downstream reactor. This introduction is carried out by any means known to those skilled in the art, directly into the reaction chamber in one embodiment or into the recirculation loop used for the cooling step e) in another embodiment.

In the first embodiment, advantageously, in order to ensure uniform mixing of the injected liquid with the liquid present in the reaction chamber, the liquid fraction originating from the upstream reactor in the cascade is introduced with a means for dispersing the injected liquid phase in the liquid phase present in the reaction chamber.

In the second embodiment, advantageously, a dispersion element is used to ensure the mixing of the liquid injected into the recirculation loop, by any means known to those skilled in the art.

Step e) of Cooling the Liquid Fraction

The process according to the invention comprises a step e) of cooling said first, "main", liquid fraction withdrawn in step c).

Preferably, the cooling step is carried out by the circulation of said first main liquid fraction withdrawn in step c) through one or more heat exchangers located inside or outside the reaction chamber, and preferably outside.

The heat exchanger advantageously makes it possible to reduce the temperature of the liquid fraction by 2 to 10° C., preferably by 3 to 9° C., preferably by 4 to 8° C. Advantageously, the cooling of the liquid fraction makes it possible to keep the temperature of the reaction medium within the desired temperature ranges.

Advantageously, carrying out the step of cooling the liquid via the recirculation loop also makes it possible to carry out the stirring of the medium and thus to homogenize the concentrations of the reactive entities throughout the liquid volume of the reaction chamber.

Step f) of Introducing the Cooled Liquid Fraction

The process according to the invention comprises a step f) of introducing the liquid fraction cooled in step e) for each reactor n.

For each reactor n, the cooled liquid fraction resulting from step e) is introduced into the gaseous part of the reaction chamber, preferably at the top of said chamber, by any means known to those skilled in the art.

Preferably, the flow rate of introduction of the cooled liquid fraction is between 500/N and 10 000/N t/h, and preferably between 800/N and 7000/N t/h, where N is the number of reactors of the cascade.

The effluent of the oligomerization process corresponds to the liquid part withdrawn from the final reactor of the cascade, which is not conveyed to the heat exchanger. At the outlet of the final reactor of the cascade, the products resulting from the reaction and also the solvent contained in the effluent may subsequently be separated, for example by distillation.

Oligomerization Reaction Device

Numerous reactors employing a gas/liquid mixture consist of a reaction chamber comprising a liquid phase and a gas phase and a loop for recirculation of a liquid fraction towards a heat exchanger enabling the cooling of the liquid fraction before injection thereof into the main chamber. Commonly, the high flow rate circulating in the recirculation loop makes it possible to obtain good homogenization of the concentrations and to control the temperature in the liquid fraction within the reaction chamber.

The reaction device employed by the process according to the invention belongs to the field of gas/liquid reactors commonly referred to as bubble point reactors. In particular, the reaction device according to the invention comprises a cascade in series of N stirred gas/liquid reactors, each of the reactors comprising the following elements:

- a reaction chamber i), of elongated shape along the vertical axis, comprising a liquid phase comprising and preferably consisting of the products of the reaction, dissolved ethylene, the catalytic system and an optional solvent, and a gas phase located above said liquid phase, comprising unreacted ethylene and also the non-condensable gases (especially methane),
- an optional means for introducing ethylene ii), located in the lateral lower part of said reaction chamber, employing a means for distributing ethylene within said liquid phase of the reaction chamber, the feeding of gaseous ethylene being active in all the reactors of the cascade, or only in a certain number of said reactors,
- an optional means for introducing the catalytic system iii), comprising at least one metal precursor, at least one activator and at least one additive, said means being located in the lower part of the reaction chamber, a liquid recirculation loop iv) comprising withdrawal means at the base (preferably at the bottom) of the reaction chamber for withdrawing and conveying a first part of the liquid fraction towards a heat exchanger enabling the cooling of said liquid, and a means for introducing said cooled liquid, said introduction being made into the gas phase at the top of the reaction chamber,
- each reactor of the cascade, except for the first, being fed by a second part of the liquid fraction withdrawn from the reactor upstream in the cascade, by feeding means v), which may be a pipe directly feeding the reaction chamber in one embodiment, or a pipe joining the recirculation loop used for the cooling step e) in another embodiment,
- the first reactor of the cascade always being fed with catalytic system and with gaseous ethylene.

i) A reaction Chamber

According to the invention, any reaction chamber known to those skilled in the art and capable of carrying out the oligomerization process can be envisaged. Preferably, the reaction chamber is of cylindrical shape and exhibits a height to width ratio (denoted H/D) between 1 and 8, preferably between 1 and 4.

Preferably, the reaction chamber comprises a means for bleeding off the non-condensable gases.

Preferably, the reaction chamber also comprises a pressure sensor which makes it possible to keep the pressure within the reaction chamber constant. Preferably, said pressure is kept constant by introducing additional ethylene into the reaction chamber.

Preferably, the reaction chamber also comprises a liquid level sensor; said level is kept constant by adjusting the flow rate of the effluent withdrawn in step c). Preferably, the level sensor is located at the interphase between the liquid phase and the gas headspace.

ii) A Means for Introducing Ethylene

According to the invention, and if the reactor n belongs to the reactors fed with gaseous ethylene of the cascade, the reaction chamber i) of said reactor n comprises a means for introducing gaseous ethylene located in the lower part of said chamber, more particularly in the lateral lower part.

Preferably, the final reactor of the cascade does not comprise a means for introducing gaseous ethylene.

Preferably, the means ii) for introducing ethylene is chosen from a pipe, a network of pipes, a multitubular distributor, a perforated plate or any other means known to those skilled in the art.

In a particular embodiment, the means for introducing ethylene is located in the recirculation loop iv).

Preferably, a gas distributor, which is a device which makes it possible to disperse the gas phase uniformly over the entire liquid section, is positioned at the end of the introduction means ii) within the reaction chamber i). Said device comprises a network of perforated pipes, the diameter of the orifices of which is between 1 and 12 mm, preferably between 3 and 10 mm, in order to form ethylene bubbles in the liquid of millimetric size.

Preferably, the velocity of the ethylene at the outlet of the orifices is between 1 and 30 m/s. Its superficial velocity (mean velocity over the total cross section of the reaction chamber) is between 0.5 and 10 cm/s and preferably between 1 and 8 cm/s.

iii) A Means for Introducing the Catalytic System

According to the invention, for at least the first reactor of the cascade, the reaction chamber i) comprises a means for introducing iii) the catalytic system.

Preferably, the introduction means iii) is located on the lower part of the reaction chamber and preferably at the bottom of said chamber.

According to a variant embodiment, the catalytic system is introduced in the recirculation loop.

The means for introducing iii) the catalytic system is chosen from any means known to those skilled in the art and is preferably a pipe.

In the embodiment in which the catalytic system is employed in the presence of a solvent or of a mixture of solvents, said solvent is introduced by an introduction means located in the lower part of the reaction chamber, preferably at the bottom of the reaction chamber or else in the recirculation loop.

iv) A recirculation Loop

According to the invention, the homogeneity of the liquid phase and also the regulation of the temperature within each of the reaction chambers are produced by using a recirculation loop comprising at least one withdrawal means on the lower part of the reaction chamber, preferably at the bottom, for withdrawing a liquid fraction towards one or more heat exchangers enabling the cooling of said liquid, and a means for introducing said cooled liquid into the gas headspace at the top of the reaction chamber.

Preferably, the means for withdrawing the liquid fraction is a pipe.

The heat exchanger(s) capable of cooling the liquid fraction is (are) chosen from any means known to those skilled in the art.

Advantageously, the recirculation loop enables good homogenization of the concentrations and makes it possible to control the temperature in the liquid fraction within the reaction chamber.

v) Liquid Feeding Means

For each reactor 2 to N of the cascade (i.e. with the exception of the first reactor of the cascade), liquid feeding means enable the introduction of the second part of the liquid fraction withdrawn from the reactor upstream in the cascade. These feeding means v) may be a pipe directly feeding the reaction chamber in one embodiment, or a pipe joining the recirculation loop used for the cooling step e) in another embodiment.

The device according to the invention preferably consists of a cascade of 2 to 10 gas/liquid reactors, preferably a cascade of 2 to 8 reactors, preferably a cascade of 3 to 8 reactors, preferably a cascade of 2 to 6 reactors, preferably a cascade of 3 to 6 reactors, preferably 2, 3, 4 or 5 reactors. The number of these reactors which are fed with gaseous ethylene represents between 25% and 100% of the total number of reactors in the cascade, preferably between 50% and 100%.

One advantage of the present invention is thus that of making it possible to achieve selectivities for olefins which are superior to those achieved with a device according to the prior art comprising only a single gas/liquid reactor, while retaining a high level of conversion of the gaseous ethylene into linear olefins and preferably into linear alpha-olefins.

EXAMPLES

The examples below illustrate the invention without limiting the scope thereof.

Example 1 (Comparative)

Example 1 illustrates the reference case corresponding to FIG. 2, in which the oligomerization process employs a single stirred gas/liquid reactor.

The example consists of a conventional stirred gas/liquid reactor for the oligomerization of ethylene, with a reaction volume in the chamber of 175 m$^3$, operated at a temperature of 135° C. and a pressure of 5.3 MPa.

The overall residence time in the reactor is 16.43 min.

The catalytic system introduced into the reaction chamber is a chromium-based catalytic system containing a content of 5 ppm of chromium, as described in patent FR 3 019 064, in the presence of a solvent, cyclohexane. This value is retained for the following examples.

The volumetric productivity of this reactor is 178 kg of alpha-olefin produced per hour and per m$^3$ of reaction volume.

The performance qualities of this reactor make it possible to convert 50.80% of the injected ethylene and to achieve a selectivity of 89.50% for the desired alpha-olefin, for a content by weight of solvent of 3.7. Said content of solvent is calculated as the weight ratio of the flow rate of injected solvent to the flow rate of injected gaseous ethylene.

Example 2 (According to the Invention)

The example consists of a cascade in series of 4 stirred gas/liquid reactors for the oligomerization of ethylene, according to the invention (see FIG. 3). The catalytic system introduced into the reaction chamber of the first reactor is a chromium-based catalytic system as described in Example 1.

The reaction volume of each one is 45.7 m$^3$. They are all operated at a temperature of 135° C. and a pressure of 5.3 MPa.

The overall residence time in the reactor cascade is 17.5 min.

The volumetric productivity of this reaction device is 171 kg of alpha-olefin produced per hour and per m$^3$ of reaction volume.

The performance qualities of this reaction device according to the invention make it possible, with the same conversion of injected ethylene (50.80%) and for the same content by weight of solvent (3.7), to achieve a superior level of selectivity for alpha-olefin than in the previous case, which reaches 90.9%, i.e. a gain of 1.4%, which is significant at this high level of selectivity, and which indicates a large gain in performance, illustrating the benefit of the device according to the invention having several gas/liquid reactors in cascade.

Example 3 (According to the Invention)

The example consists of a cascade in series of 4 stirred reactors for the oligomerization of ethylene, in an embodiment corresponding to FIG. 4: 3 gas/liquid reactors followed by a 4th reactor without injection of gaseous ethylene, according to the invention.

The reaction volume of each one is 46.6 m$^3$. They are all operated at a temperature of 135° C. and a pressure of 5.3 MPa.

The overall residence time in the reactor cascade is 14.6 min.

The volumetric productivity of this reaction device is 168 kg of alpha-olefin produced per hour and per m³ of reaction volume.

The performance qualities of this reaction device according to the invention make it possible, with the same conversion of injected ethylene (50.80%) and at a content by weight of solvent of 3.85, to achieve a yet further superior level of selectivity for alpha-olefin than in the previous case, which reaches 91.2%, illustrating the benefit of the invention.

Example 4 (According to the Invention)

The example consists of a cascade in series of 4 stirred reactors for the oligomerization of ethylene: 3 gas/liquid reactors followed by a 4th reactor without injection of gaseous ethylene, in the embodiment corresponding to FIG. 4 according to the invention.

The reaction volume of each of these reactors in this example is 48.9 m³. They are all operated at a temperature of 135° C. and a pressure of 5.3 MPa.

The overall residence time in the reactor cascade is 25.41 min.

The volumetric productivity of this reaction device is 160 kg of alpha-olefin produced per hour and per m³ of reaction volume.

The performance qualities of this reaction device according to the invention make it possible, with the same selectivity for alpha-olefin (89.50%), to improve the conversion of the injected ethylene from 50.8% to 66.45%, while reducing the content by weight of solvent from 3.7 to 3.45, illustrating the benefit of the invention.

The invention claimed is:

1. A process comprising selective oligomerization of ethylene to give a linear alpha-olefin, carried out at a pressure of between 0.1 and 10 MPa, at a temperature of between 30 and 200° C., in a cascade of N gas/liquid reactors in series, N being at least equal to 4, comprising the following:
   a. introducing a homogeneous catalytic oligomerization system comprising at least one metal precursor, optionally at least one activator and optionally at least one additive into at least the first reactor of the cascade,
   b. bringing said homogeneous catalytic system and an optional solvent into contact with ethylene by introducing said ethylene into the lower part of the reaction chamber of each of the N reactors of the cascade, with the exception of the last reactor in the cascade,
   c. for each reactor n, withdrawing a liquid fraction in the lower part of the reaction chamber of the reactor n, the liquid fraction being separated into two streams: a first stream corresponding to a first part of the liquid fraction, which is conveyed to a heat exchanger for cooling; a second stream corresponding to the second part of the liquid fraction which constitutes the liquid feedstock of the following reactor n+1 in the cascade,
   d. introducing said second part of the liquid phase withdrawn from the reactor n towards the reaction chamber of the following reactor n+1 in the direction of flow, comprising a liquid phase and a gas phase,
   e. cooling said first part of the liquid fraction withdrawn from the reactor n in c) by passing said first part of the liquid fraction into a heat exchanger in order to obtain a cooled liquid fraction,
   f. introducing said liquid fraction cooled in e) at the top of the reaction chamber of said reactor n, a) to f) being carried out, unless indicated otherwise, for each reactor n of the cascade, n being between 1 and N.

2. The process according to claim 1 wherein, for the final reactor N of the cascade, said second part corresponds to the effluent obtained at the end of the oligomerization process and is conveyed to a separation section to separate the linear olefins produced.

3. The process according to claim 1, wherein a solvent or a mixture of solvents is introduced only into the first reactor of the cascade.

4. The process according to claim 1, wherein the content by weight of solvent introduced into the cascade of reactors is between 0.5 and 10.0.

5. The process according to claim 1, wherein, in c), the flow rate of said second stream is 5 to 200 times lower than the liquid flow rate of the first stream conveyed to the cooling step.

6. The process according to claim 1, wherein the cascade comprises from 4 to 10 gas/liquid reactors.

7. The process according to claim 1, wherein the flow rate of the liquid recirculation loop of each reactor is between 500/N and 10 000/N t/h, where N is the number of reactors in the cascade.

8. The process according to claim 1, wherein the concentration of catalyst in the catalytic system is between 0.1 and 50 ppm by weight of atomic metal relative to the reaction mass.

9. The process according to claim 1, wherein the catalytic oligomerization reaction is carried out continuously.

10. The process according to claim 1, wherein, in f), the introduction flow rate of the cooled liquid fraction is between 500/N and 10 000/N t/h, where N is the number of reactors in the cascade.

11. The process according to claim 1, wherein the linear olefins obtained have 4 to 12 carbon atoms.

12. The process according to claim 11, wherein the linear olefins obtained are linear alpha-olefins but-1-ene, hex-1-ene or oct-1-ene.

13. A device carrying out the process for the oligomerization of ethylene according to claim 1, comprising a cascade of N stirred gas/liquid reactors, each of the N reactors comprising:
   a reaction chamber i), of elongated shape along the vertical axis, comprising a liquid phase, dissolved ethylene, the catalytic system and an optional solvent, and a gas phase located above said liquid phase, comprising unreacted ethylene and also the non-condensable gases;
   an optional inlet introducing ethylene ii), located in the lateral lower part of said reaction chamber, employing a distributor distributing ethylene within said liquid phase of the reaction chamber, the feeding of gaseous ethylene being always active in the first reactor of the cascade;
   an optional inlet introducing the catalytic system iii) comprising at least one metal precursor, optionally at least one activator and optionally at least one additive, said inlet being located in the lower part of the reaction chamber, the introduction of the catalytic system being always carried out in the first reactor of the cascade and in the following reactors;
   a recirculation loop iv) comprising at least one withdrawal outlet at the base of the reaction chamber for withdrawing and conveying a first part of the liquid fraction towards a heat exchanger enabling the cooling of said liquid fraction, and an inlet introducing said cooled liquid fraction into the gas phase at the top of the reaction chamber, an inlet feeding liquid v) by the second part of the liquid fraction withdrawn from the reactor upstream in the cascade, except for the first reactor of the cascade.

\* \* \* \* \*